United States Patent [19]

DiMartino

[11] Patent Number: 5,300,781
[45] Date of Patent: Apr. 5, 1994

[54] NON-HYDROGENOUS PROCESS LEVEL MEASUREMENT

[75] Inventor: John M. DiMartino, Chicago, Ill.

[73] Assignee: Kay-Ray/Sensall, Inc., Mount Prospect, Ill.

[21] Appl. No.: 804,355

[22] Filed: Dec. 9, 1991

[51] Int. Cl.⁵ .................. G01N 23/09; G01T 3/00; G01F 23/00
[52] U.S. Cl. .................. 250/357.1; 250/390.04; 250/390.06; 250/391
[58] Field of Search .................. 200/390.06, 390.04, 200/357.1, 391, 390.10

[56] References Cited

U.S. PATENT DOCUMENTS

| | | |
|---|---|---|
| 2,378,219 | 6/1945 | Hare .................. 250/357.1 |
| 2,873,377 | 2/1959 | McKay . |
| 2,967,937 | 1/1961 | McKay . |
| 3,099,745 | 7/1963 | Borst . |
| 3,350,561 | 10/1967 | Dresia et al. . |
| 3,524,062 | 8/1970 | Rocoplan et al. . |
| 3,532,883 | 10/1970 | Dresia et al. . |
| 4,038,548 | 7/1977 | Charlton .................. 250/357.1 |
| 4,152,590 | 5/1979 | Smith, Jr. et al. . |
| 4,241,253 | 12/1980 | Allen et al. . |
| 4,243,886 | 1/1981 | Untermyer, II . |
| 4,270,051 | 5/1981 | Galkin et al. .................. 250/358 R |
| 4,358,682 | 11/1982 | Telfer et al. .................. 250/390.01 |
| 4,369,368 | 1/1983 | Bernard et al. .................. 250/357.1 |
| 4,395,633 | 7/1983 | Mathew . |
| 4,582,992 | 4/1986 | Atwell et al. .................. 250/357.1 |
| 4,794,256 | 12/1988 | DiMartino et al. .................. 250/357.1 |
| 4,870,278 | 9/1989 | Leonardi-Cattolica et al. .................. 250/390.06 |
| 4,918,315 | 4/1990 | Gomberg et al. . |
| 4,938,916 | 7/1990 | Dance . |
| 5,078,951 | 1/1992 | August, Jr. .................. 250/392 |
| 5,099,124 | 3/1992 | Benson .................. 250/390.06 |

Primary Examiner—Carolyn E. Fields
Assistant Examiner—Drew A. Dunn
Attorney, Agent, or Firm—Westman, Champlin & Kelly

[57] ABSTRACT

A process measurement system that utilizes fast neutron backscattering for measuring density, level, and interfaces of substantially non-hydrogenous materials. The present invention substantially expands the use of backscattering technology, by expanding measurement to materials other than those containing hydrogen, and allowing measurement of materials in thicker walled vessels than previously possible. The system contains a fast neutron source for emitting neutrons into the material to be measured. The detection system is mounted near the neutron source to receive the backscattered neutrons. An energy degradation system is also incorporated to reduce the energy level of the fast neutrons down to a desired range.

15 Claims, 3 Drawing Sheets

NON-HYDROGENOUS PROCESS LEVEL MEASUREMENT

BACKGROUND OF THE INVENTION

The present invention relates to the measurement of levels, phase, interfaces, and density of substantially non-hydrogenous process materials using neutron backscattering for measurements.

The use of thermal neutron backscatter, thermal neutron transmission, fast neutron transmission, and various gamma radiation techniques for process measurements have long been known. For example, the assignee of the present application, Kay-Ray Sensall Inc., of Mount Prospect, Ill., has level and interface measurement systems using radiation sources in detection, such as their Model 4800X Level System, the Model 4760 Level System, the Model 4160 Neutron Level/Interface Measurement System, and the Model 3660 Density Measurement System. These systems use radiation principles, having sources of radiation and detectors, which provide an output indicating a level of process material. The detection circuitry senses the output and uses it for control of a process, for example, with microprocessor control and two or four wire transmitter systems.

Fast or high energy neutron sources are known, and are used in measurement systems, such as in moisture detectors and interface level measurements. Fast neutrons may be converted to thermal neutrons when they travel in certain materials, especially hydrogen containing materials. Detection of either backscattered or transmitted thermal neutrons is the basis of such measurements. Thermal neutron detection systems are readily and inexpensively applied to hydrogenous process measurements. These detection systems are extremely limited in their detection of neutron energies above the thermal or epithermal range. The detection probability of these detection systems at above epithermal energies is only 1/100 of a percent of the capture probability at the thermal energies.

A system that uses direct measurement of the quantity of transmitted high energy or fast neutrons is the assignees Model 4360 Neutron Transmission System, the principles of which are disclosed in U.S. Pat. No. 4,794,256, titled FAST NEUTRON PROCESS MEASUREMENT SYSTEM.

The apparatus of the present invention detects backscattered neutrons having above epithermal energy, as opposed to measuring transmission of neutrons. A greatly reduced neutron source size can also be used in the present invention since the neutrons need not be transmitted through the entire vessel filled with the process material.

The present system measures density, level and interfaces of non-hydrogenous as well as hydrogenous materials based on neutron backscatter techniques. The invention expands the accurate measurement to materials that are either totally devoid of hydrogen or contain only trace amounts of hydrogen. Moderation of fast neutrons to thermal neutrons by hydrogen contained in the process material being monitored, is no longer a requirement and therefore not a limitation for the application of neutron backscatter to process measurements.

The invention allows cost effective application of neutron backscatter measurements to a broad new field of non-hydrogenous process materials. The ability to apply neutron backscatter instrumentation to process measurements that contain any element as opposed to only those that contain hydrogen substantially expands the use of the technology. Measurement error due to thermal neutron capture by high barns value elements is greatly reduced due to the energy detection spectrum of the invention.

Another benefit of the system in the present invention is that it is non-contacting and non-intrusive. Thus, it is not adversely affected by high temperatures or pressures, chemical corrosion, abrasion or other factors that adversely affect internal or contacting measurement systems.

When compared to thermal neutron backscatter systems, the present invention has significantly greater penetration through vessel walls. In thermal neutron systems interaction with the hydrogen contained in the process material readily reduces the neutrons to sub-epithermal ranges. After thermalization the neutron must traverse that portion of the process material that lies between the vessel and the point of thermalization, in addition to the vessel wall to reach the detectors. At thermal energies the maximum steel vessel wall thickness for process measuring is less than 3 inches. In the present invention, measurements can be made on vessels with a maximum thickness of 4 inches of steel or equivalent in refractory brick or other materials.

By way of comparison, thermal neutrons are considered to be neutrons having an energy level below 0.025 electron volts; epithermal neutrons have energy levels between 0.025 and 100 electron volts while the preferred fast neutrons emitted from the source with a mean energy level of over four million electron volts.

Another aspect of the system is that generally neutrons do not occur naturally as background radiation, thus it is practical to use small source sizes and detect the resulting low quantities of backscattered neutrons. Gamma radiation based systems must overcome a natural occurring gamma background radiation, which requires raising the total radiation level.

SUMMARY OF THE INVENTION

The invention relates to a measurement system utilizing fast neutron backscattering for measuring material levels or other parameters of substantially non-hydrogenous material in a walled vessel. The source of fast neutrons mounts in a way to direct high energy, or fast, neutrons into the walled vessel. The detection system mounts near the neutron source to receive neutrons scattered back toward the source as a result of collisions with nuclei of material in the vessel. An energy degradation shield, or moderator, also mounts between the neutron source and the vessel to provide for selected energy degradation to enhance detectable backscatter so measurement signal levels are high.

Moderator, or moderation, is commonly used to define the slowing down of high velocity neutrons. Moderation is, however, often associated with the total slowing down, or attempt to do so, of neutrons to their terminal velocity at the thermal energy in a single step, and therefore not consistent with the present invention. The term energy degradation shield is used here to imply the controlled and managed neutron energy reduction to the thermal range to match the process measurement to be accomplished.

In one preferred embodiment the neutron source and the detection system are housed in one assembly. In this embodiment, the energy degradation shield is in front of both the source and detection system to provide energy degradation to aid in the detectable backscatter resulting from the non-hydrogenous process material.

DETAILED DESCRIPTION OF THE PREFERRED EMBODIMENTS

Figure 1:
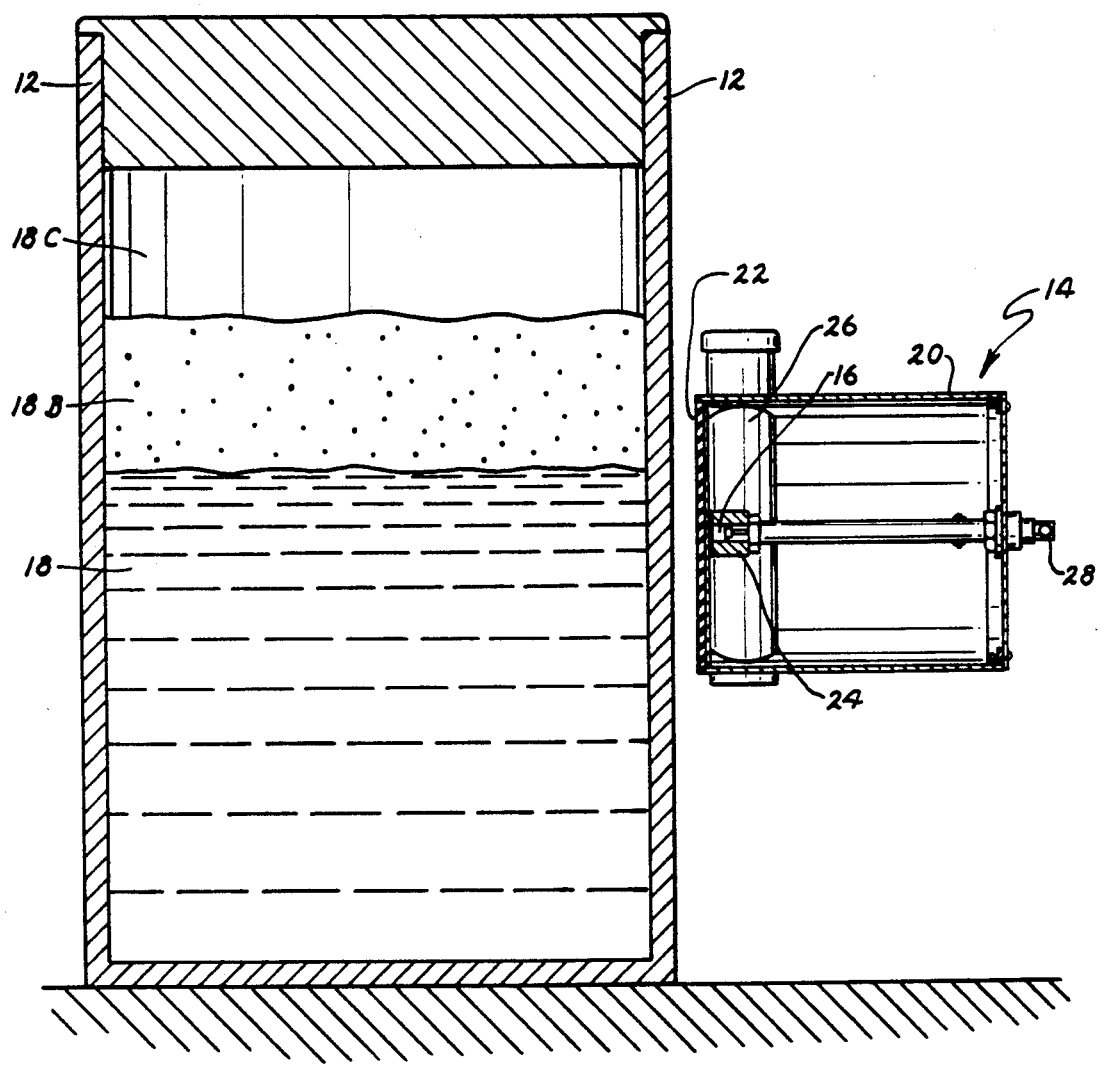
FIG. 1 is a side elevational view of the source and measuring unit mounted on the side of a process vessel containing a process material.

As shown in FIG. 1 a thick walled vessel indicated generally at 10 has walls 12 made of steel. Shown on one side of vessel 10 is a preferred embodiment of the measuring unit, indicated generally at 14. In the embodiment shown, a fast or high energy neutron source 16 directs the high energy neutrons through wall 12 into process material 18. The vessel can be a catalyst bed container in which a dense bed 18 is near the bottom and interfaces with a transition zone 18B which in turn has a vapor phase zone 18C. The present invention has the capability of determining density and interface levels between the zones and phases.

In the preferred embodiment the fast neutron source 16, is a 500 milli-Curie (mCi) AmBe source of known design. Other sources such as, Cf$^{252}$ or Pu$^{244}$ Be, can also be used. A lead gamma shield 24 encircles the neutron source to absorb the low level gamma radiation emitted from the source 16.

Figure 2:
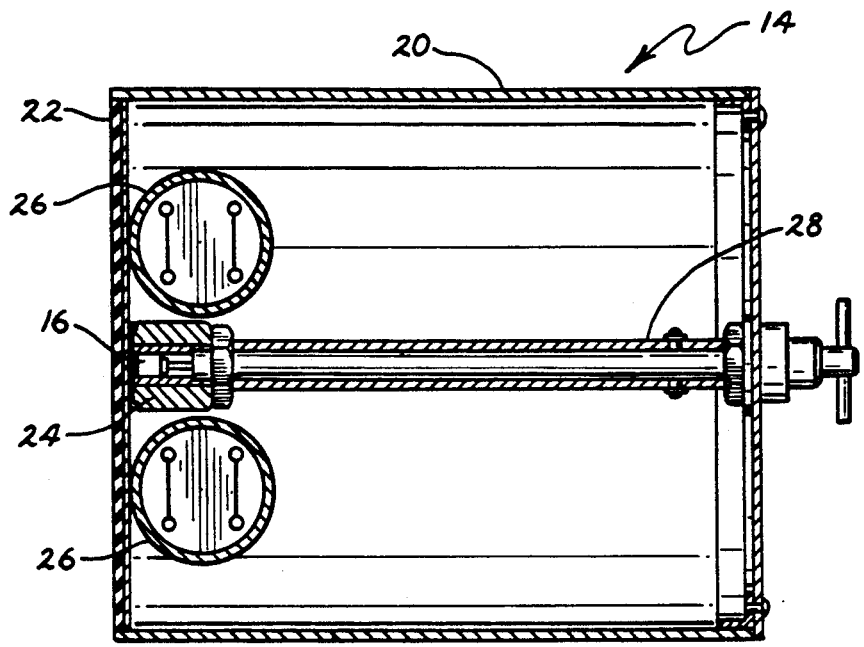
FIG. 2 is a top sectional view of the measuring unit of FIG. 1.

The neutron measuring unit 14 shown generally in FIG. 1 and FIG. 2 is enclosed by a housing 20. An energy degradation shield 22 is between the housing 20 and the wall 12 of vessel 10. Also enclosed in the housing 20 are the detectors 26 and the lead gamma shield 24. Extending through the housing 20 is a securing rod 28 that protrudes out of the rear of the housing 20. The neutron source 16 is secured to the end of the securing rod 28, and the rod 28 is used to physically move the source 16 from the measuring position (as shown) to the store position in the center of the housing 20. The energy degradation shield 22 is a hydrogen containing material which can be a plastic of selected chemical composition and hydrogen density. The energy degradation shield 22 can also be made of any other material known to reduce neutron energies such as carbon.

Placing the fast neutron source 16 and detector means 26 in a single enclosure or housing allows for detecting backscattered neutrons as opposed to transmitted neutrons. A greatly reduced neutron source size can be used since the neutrons need not be transmitted through the entire vessel containing the process material and through two wall thicknesses.

Figure 3:
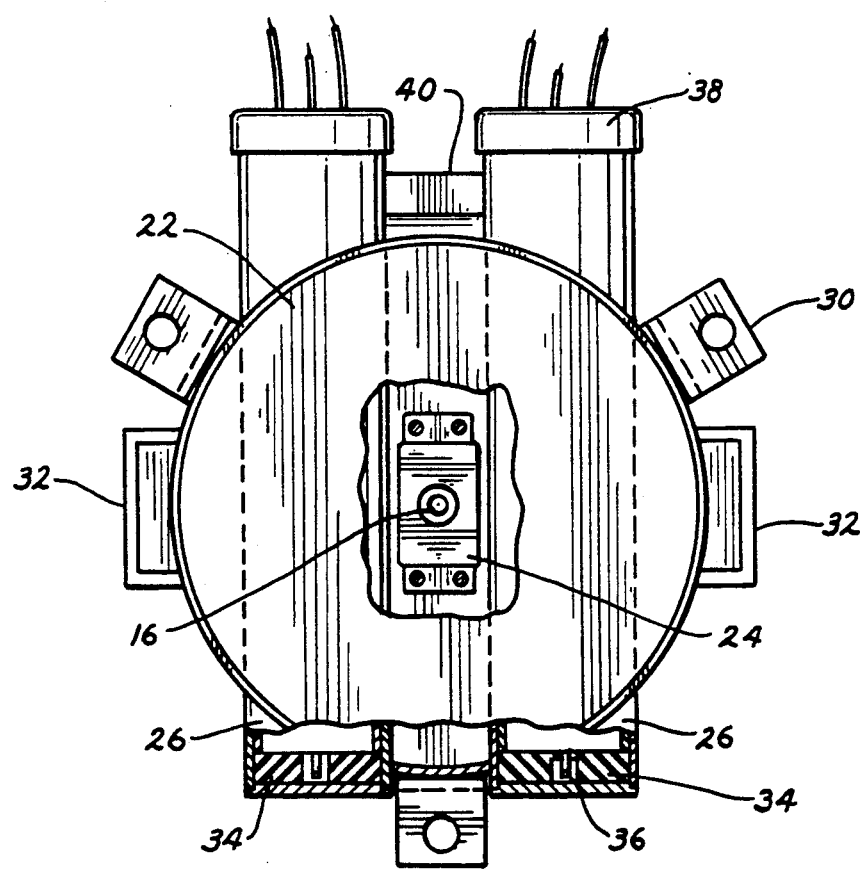
FIG. 3 is an end elevational sectional view taken along line 3—3 in FIG. 2.

FIG. 3 shows the vertical view of the measuring unit along the line 3—3 from FIG. 2. Included in FIG. 3 are attachment clips 30, lift handles 32, insulator material 34, bolts 36, end caps 38, and wire conduit 40. The detectors 26 have terminals which carry a signal that is indicative of the detected neutrons. The remote circuitry (not shown) uses the signal for providing information about the parameter being detected. It is desirable to use thermal or low energy neutron detectors because of their availability, and reliability. Reducing the energy of the fast neutrons into the thermal or epithermal range is needed for detection by the detectors.

Neutrons undergo energy degradation in collisions with nuclei. This principle is the basis of all backscatter measurements. The aggregate actions of neutron collisions is referred to as scattering. Neutron scattering falls into two types, elastic and inelastic.

The term elastic scattering is defined as the scattering fast neutrons undergo when they collide with hydrogen nuclei. Inelastic scattering is defined as the scattering fast neutrons undergo with nuclei other than hydrogen. "Fast neutrons" is a relative phrase due, in part, to the broad energy spectrum emitted by most commercially available sources such as Am241:BE or Cf252, but is defined here as neutrons above one kiloelectron volt.

Hydrogen has the greatest ability to degrade a fast neutron to the thermal energy range. All other elements have a greatly diminished ability to thermalize neutrons when compared to hydrogen.

Neutrons that are backscattered from non-hydrogenous materials create very few neutrons in the epithermal or thermal ranges for detection purposes. Fast neutrons, normally the result of inelastic scattering being returned to thermal neutron detectors, are not captured and the process data associated with inelastic scattered neutrons is lost. Therefore, current technology seriously restricts the use of a valuable measurement technology by industrial processors.

Inelastic scattering occurs in hydrogen based measurements from the non-hydrogenous constituents of the process but is not detected by the thermal neutron detectors commonly employed. Neutrons that undergo inelastic scattering either are degraded to the thermal energy range by additional collisions with hydrogen, and detected and interpreted as solely hydrogen related interactions, or are scattered back to the detectors and not detected due to their high energy. In processes that do not contain hydrogen, only inelastic collisions occur in significant numbers. Multiple inelastic neutron/nucleus collisions can reduce a neutron to the thermal energy range, which can then be detected by typical thermal neutron backscatter systems. However, statistically too few of these thermal neutrons are produced to be used in real time process measurements.

In the present invention, fast neutrons emitted from the source 16 pass through the energy degradation shield 22 which is selected to lower the mean neutron flux energy to a desired level. Preferably, the mean energy is still in the lower portion of the fast neutron range after passing through the shield 22 toward the vessel 10. The neutrons then pass through the vessel wall 12 into the process material 18. A significant quantity of the neutrons collide with the nuclei of the process material 18 and undergo inelastic scattering. The inelastic scattering slightly degrades the neutrons' energy. Those neutrons that scatter back through the vessel wall 12 once again pass through the hydrogen rich energy degradation shield 22 and their energy degrades again to the detectable thermal or epithermal range. The neutrons are then captured or sensed by the thermal neutron detectors 26.

Any thermal neutron detectors can be used for the system measurements. The detectors 26 used in the preferred embodiment are gas filled cylinders, such as boron trifluoride ion chambers, which are known to persons skilled in the art. The output of the detectors 26 is directly proportional to the neutrons received. The detectors output is then sent to the processing electronics, which is not shown.

The invention uses three factors in the detection of the inelastically backscattered neutrons. The first factor is a three stage neutron energy degradation sequence employed to exploit the inelastic scattering which occurs with non-hydrogenous process material. The first stage of energy degradation is the result of a controlled number of elastic collisions with hydrogen. The thickness of the energy degradation shield and/or selection of the material used, controls the number of collisions and the corresponding energy reduction. Plastics of varying chemical composition and hydrogen density are preferred. One quarter inch of polyethylene has been experimentally found to be a satisfactory shield. If the energy degradation in this first stage is too great, the mean flux energy of the neutrons entering the vessel drops to the thermal range, and measurement sensitivity is greatly reduced.

The second energy degradation stage comprises collisions of the neutrons emitted with the non-hydrogenous process elements resulting in inelastic scattering which causes a moderate mean flux energy reduction. The final energy reduction occurs as the neutrons again pass through the energy degradation shield 22 and degrade to the thermal and epithermal range where the detectors 26 have the highest probability of capture.

The second factor used in the detection of backscattered neutrons is optimum geometry. Since stage two of the energy degradation sequence is not highly efficient, due to low probability of inelastic collisions, the source 16 and detector 26 arrangement must maximize the probability of intercepting backscattered neutrons from the process material. Placement of the source 16 physically between the detectors 26 reduces the distance from the collision occurrence in the process material back to the detectors.

The third factor for detection of backscattered neutrons is to maximize the collection area for the returning neutrons. The preferred neutron source is an AmBe source. Of the 1.3 million neutrons emitted per second from a 500 mCi source, only a fraction of these (approximately 3 neutrons per second per square centimeter of collection area) return from the process to be detected. Therefore, the larger the collection area, the greater the number of returning neutrons will be detected.

Two examples of the application of the invention are the density and interface level measurements on Fluid Catalytic Cracking (FCC) process in petroleum refineries. The FCC is a petroleum refining process that upgrades processed heavy oils to lighter and more valuable products. The most important FCC product is high-octane gasoline. An FCC is one of the most important and profitable units in a refinery. Differential pressure measurements commonly employed to measure the density and level of the fluidized catalyst bed are prone to measurement error and reliability. Since the catalyst is devoid of hydrogen, thermal neutron backscatter is not capable of making the interface and density measurements.

Figure 4:
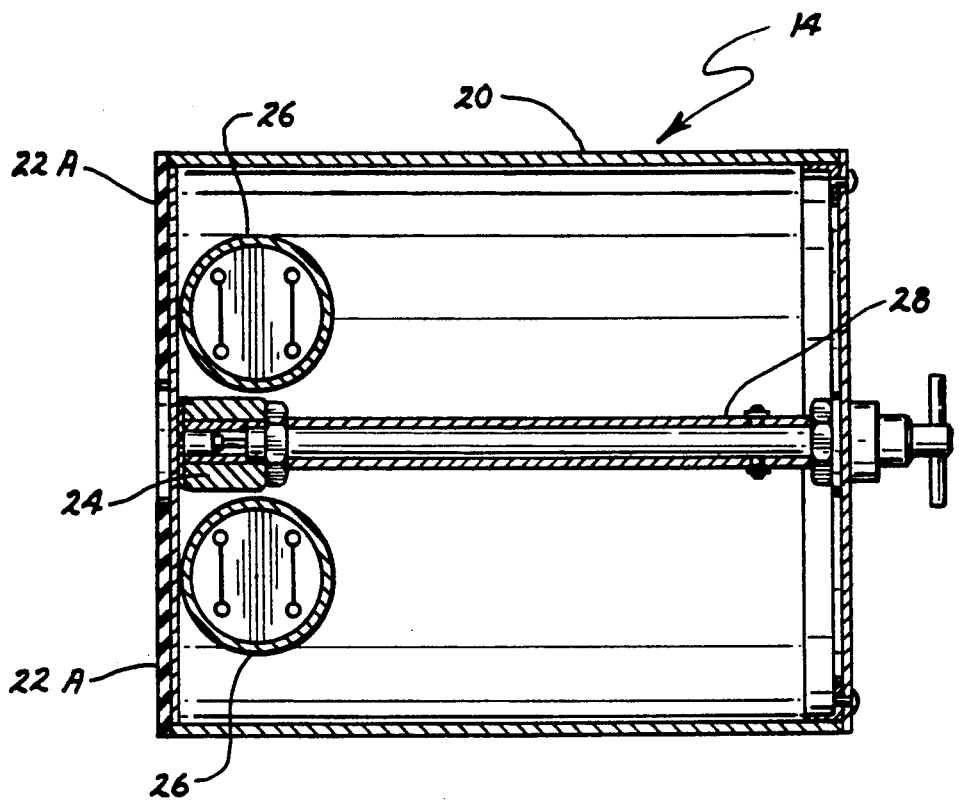
FIG. 4 is a view similar to FIG. 2 showing a modified energy degradation shield.

The invention will work by proper selection of the energy degradation shield material and thickness if only the source neutrons pass through the shield, or if the source neutrons avoid the shield and the shield is used only with backscattered neutrons. In FIG. 4, a modified energy degradation shield 22A is shown in two sections, one in front of each detector 26 so only the backscattered neutrons pass through the shield and the neutrons from the source avoid the shield.

Figure 5:
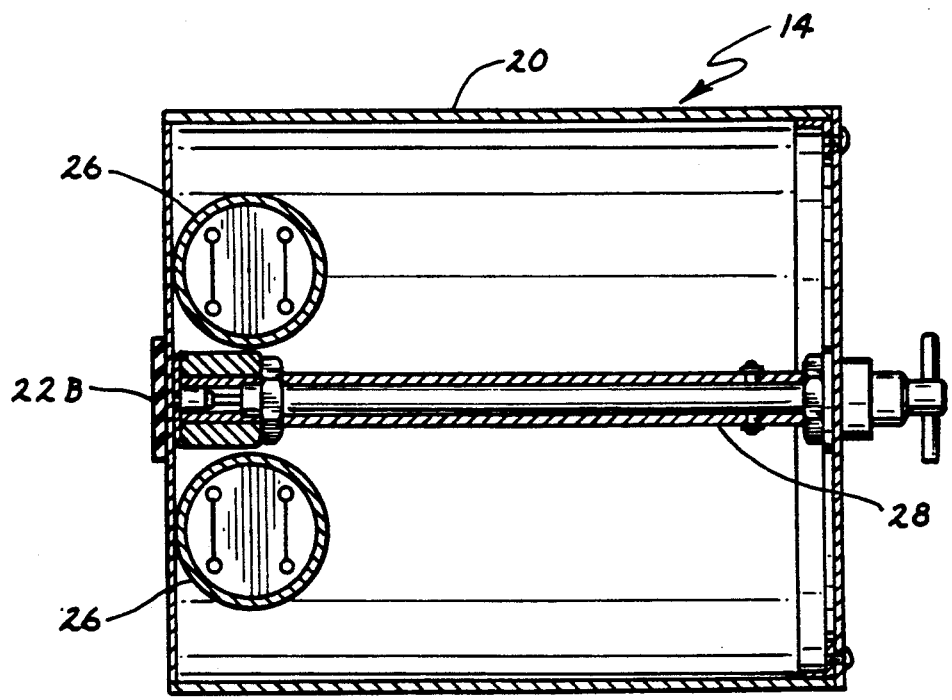
FIG. 5 is a view similar to FIG. 2 showing a further modified energy degradation shield.

In FIG. 5, a modified energy degradation shield 22B is placed between the source and the vessel only. The backscattered neutrons avoid the shield and are directly measured by the detector means 26.

Point level interface of the top of the bed is needed in addition to the differential pressure determined continuous level of the total catalyst bed. The point level interface is required to address short-falls in the differential pressure based technology commonly used to measure the continuous level.

Accurate, point level measurement of the top or the dense bed requires an instrument that can identify the interface between the dense bed 18A, the disengagement zone 18B, and vapor phase 18C.

The measurement is made by determining the density of the catalyst at a discrete point. A density measurement enables the discrimination between the dense bed, the disengagement zone and the vapor phase.

Although the present invention has been described with reference to preferred embodiments, workers skilled in the art will recognize that changes may be made in form and detail without departing from the spirit and scope of the invention.

I claim:

1. A fast neutron detection system for accurate measurement of parameters of substantially non-hydrogenous material contained in a walled vessel comprising:
    a fast neutron source comprising means for directing fast neutrons in a first direction from an exterior of the vessel through the vessel wall to the substantially non-hydrogenous material;
    a detector system mounted adjacent to the neutron source to provide detection of neutrons scattered back from the material through the vessel wall in a direction substantially opposite from the first direction; and
    an energy degradation shield disposed adjacent the source and in the path of neutrons emerging in a first direction to reduce the energy of the fast neutrons to a desired energy level for detection by the detector system.

2. The system as specified in claim 1 wherein the energy degradation shield comprises plastic material.

3. The system as specified in claim 1 further including means for positioning the shield so that the neutrons directed from the source to the material pass through the energy degradation shield, and the neutrons scattered back from the material to the detector system avoid the energy degradation shield.

4. The system as specified in claim 1 wherein the backscattered neutrons pass through the energy degradation shield and the neutrons directed from the source to the material avoid the energy degradation shield.

5. The system as specified as in claim 1 wherein both the source neutrons and the backscattered neutrons pass through the energy degradation shield.

6. System as specified in claim 1 wherein the neutron source and the detection system are housed in one enclosure.

7. The system as specified in claim 1 wherein the detection system comprises chambers with large surface areas.

8. The system as specified in claim 7 wherein the detection system comprise boron trifluoride gas filled chambers.

9. The system as specified in claim 7 wherein the neutron source is disposed between the detection system.

10. The system as specified in claim 1 wherein the neutron source comprises Americium 241 Beryllium.

11. A method of determining characteristics of a substantially non-hydrogenous material located in a walled vessel comprising the steps of:
   directing high energy neutrons from a source located outside the walled vessel to the material;
   detecting the neutrons scattered back from the material toward a detection means;
   providing an energy degradation sequence adjacent at least one of the source and the detector means to reduce the energy levels of the directed or detected neutrons to a desired range.

12. The method of claim 11 wherein the vessel walls have a maximum thickness of four inches of steel materials.

13. The method of claim 11 including the step of providing the energy degradation sequence in three stages including providing a controlled mean neutron energy reduction through elastic collisions with hydrogen and high energy neutrons, causing collisions of high energy neutrons with the substantially non-hydrogenous material, and causing a controlled number of collisions with hydrogen and low energy neutrons.

14. A fast neutron backscatter detection system for accurate measurement of characteristics substantially non-hydrogenous material contained in a walled vessel comprising:
   a fast neutron source disposed between multiple ion detection chambers;
   a gamma shield means located between the source and detection chambers for preventing gamma radiation from the source from directly striking said detection chambers; and
   an energy degradation shield positioned adjacent the neutron source and the detection chambers such that neutrons emitted from the source pass through the shield and through substantially non-hydrogenous material aligned with the source, and backscattered neutrons pass through the shield before being intercepted by the detection chambers to reduce the energy level of neutrons detected by the detection chambers substantially to the epithermal energy range and below.

15. The system as specified in claim 14 wherein said energy degradation shield comprises plastic material.

* * * * *

UNITED STATES PATENT AND TRADEMARK OFFICE
CERTIFICATE OF CORRECTION

PATENT NO. : 5,300,781
DATED : April 5, 1994
INVENTOR(S) : John M. DiMartino

It is certified that error appears in the above-indentified patent and that said Letters Patent is hereby corrected as shown below:

Column 7, line 14, cancel "detector" and insert --detection--.

Column 8, line 4, after "characteristics" insert --of--.

Signed and Sealed this

Sixteenth Day of August, 1994

Attest:

BRUCE LEHMAN

Attesting Officer     Commissioner of Patents and Trademarks